United States Patent [19]

Sachs et al.

[11] 4,185,755
[45] Jan. 29, 1980

[54] ADJUSTABLE DOSE PISTOL-TYPE APPLICATOR

[75] Inventors: Hermann W. Sachs, Leverkusen, Fed. Rep. of Germany; Peter Marek, Ciudad de Guatemala, Guatemala; Florian Dorner, Dusseldorf, Fed. Rep. of Germany

[73] Assignee: Bayer Aktiengesellschaft, Leverkusen, Fed. Rep. of Germany

[21] Appl. No.: 805,557

[22] Filed: Jun. 10, 1977

[51] Int. Cl.$^2$ .............................................. G01F 11/00
[52] U.S. Cl. ...................................... 222/43; 222/309; 222/321
[58] Field of Search ................ 222/309, 321, 324, 43; 239/333

[56] References Cited

U.S. PATENT DOCUMENTS

| 1,724,766 | 8/1929 | McCauley | 222/321 X |
| 2,805,798 | 9/1957 | Sampson | 222/309 |
| 3,118,568 | 1/1964 | Bishop et al. | 222/43 |
| 3,135,302 | 6/1964 | Ballin | 222/309 X |
| 3,474,938 | 10/1969 | Clevenger | 239/333 X |
| 3,492,876 | 2/1970 | Bull et al. | 222/309 X |

FOREIGN PATENT DOCUMENTS 655683 12/1928 France ..................................... 239/333

Primary Examiner—Robert J. Spar
Assistant Examiner—Frederick R. Handren
Attorney, Agent, or Firm—Sprung, Felfe, Horn, Lynch & Kramer

[57] ABSTRACT

A pistol applicator has a piston handle and a hand hold which are drawn towards each other during application and a piston cylinder housing. An adjustable dose regulating device is provided including a dose regulating wheel fixed to the cylinder housing and rotatable about the longitudinal axis of the cylinder housing and a plurality of notches in the dose regulating wheel each having a different radial extent. An outwardly tapering stepped cross piece is attached to the piston handle and is insertable in one preselected notch at a time, wherein one step of the crosspiece is engageable with the preselected one of the notches upon operating the applicator piston to limit the stroke thereof and thereby regulate the dose applied.

2 Claims, 4 Drawing Figures

ADJUSTABLE DOSE PISTOL-TYPE APPLICATOR

The invention relates to a pistol-type applicator for use in veterinary or botanical fields with a piston handle and a cylinder handhold which are drawn towards each other during application. Such types of pistol applicators are often equipped with an adjustable dose-regulating device.

In the known pistol applicators the dose-regulating device consists of a setscrew which limits the piston stroke according to the dosage desired. This has the disadvantage that when changing over to other dosage rates the setscrew has to be set in another position by means of a lengthy procedure.

It has been found that the adjustment of the dosage rate is in practice inconvenient and that the pistol applicator is difficult to handle.

The object of the present invention is to create a pistol applicator by means of which the dosage rate can be easily changed over from one setting to the other. At the same time the construction must be designed in such a way that the pistol applicator lends itself easily to production by means of injection moulding in order to allow cheap large scale manufacture.

According to the invention this object is fulfilled by a pistol applicator characterized in that the dose-regulating device consists of a dose-regulating wheel which is fixed to the cylinder housing, can be turned about the longitudinal axis of the cylinder and has stepped notches (recesses) of varying radial extent and a stepped crosspiece is attached to the piston handle which fits into one of the preselected notches upon operating the applicator piston.

The wheel is advantageously provided with cams which engage with corresponding grooves on the cylinder wheel to releasably hold the wheel in a selected position.

For the purpose of the innovation the cylinder has engaging grooves which correspond with the notches of varying radial extent. In this way a quick and convenient setting of the desired dosage rate is made possible.

A further advantage of the innovation is that the pistol applicator lends itself easily to production by means of injection moulding. A set of dose-regulating wheels can be made available for the user, which are appropriately made for the various indications. There is thus no longer the need, as has so far been established, for differing pistol applicators for differing types of uses. The main uses in the veterinary field are transcutaneous (spot-on), oral or rectal forms of administration of solutions or suspensions to domestic animals of all species.

In the following an example of an embodiment of the innovation is described in greater detail with the help of illustrations.

Figure 1:
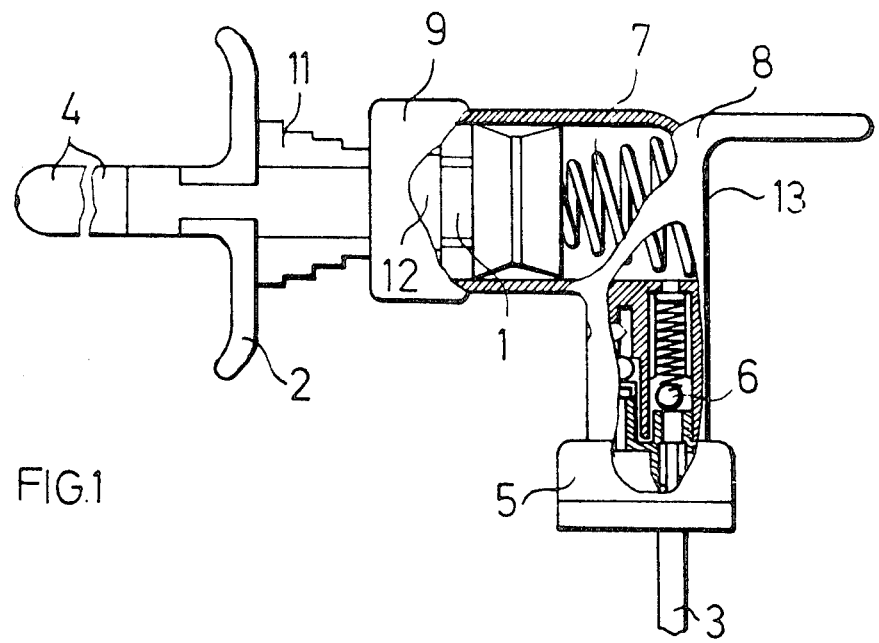
FIG. 1 shows a side and inside view of the pistol applicator.

The pistol applicator shown in FIG. 1 is a modified version of a commercially available piston applicator with two ball valves. The device is set in operation by means of suction achieved with the aid of a piston handle 2 attached to the piston 1. By pulling the piston handle and allowing the piston to return the liquid which is to be applied is sucked in via a suction feed pipe 3 from a supply container (not shown) and is ejected through the mouthpiece 4. The pistol applicator can be fixed directly to the supply container by means of the screw cap 5. The ball valve 6 prevents the liquid running back when the piston handle 2 is pulled. By means of the pressure spring 7 inside the piston chamber the piston 1 is pushed back into the starting position after application is completed, while the ball valve in the piston handle closes.

Figure 2:
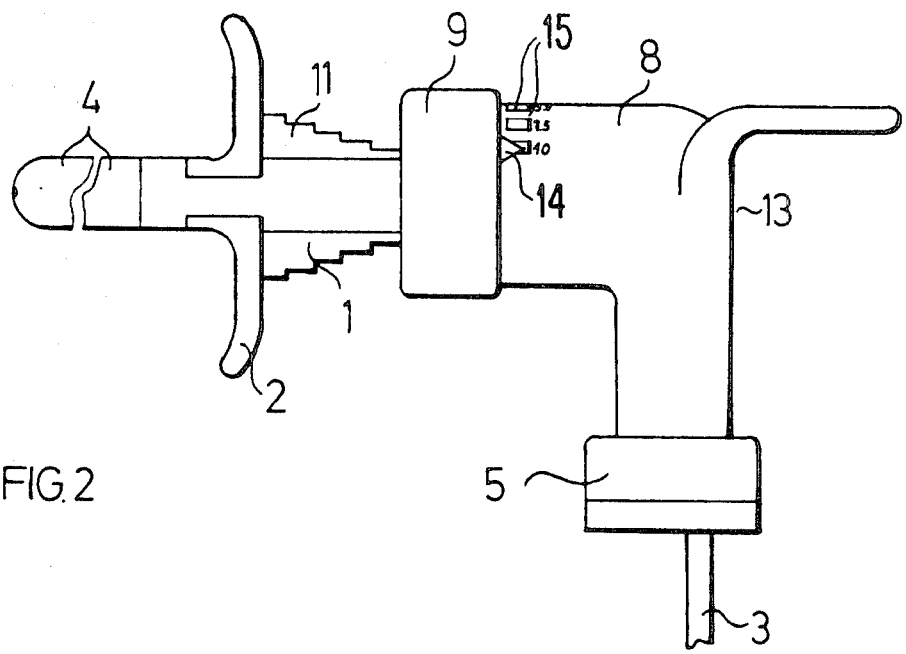
FIG. 2 shows a side view with the dose-regulating wheel.
Figure 3:
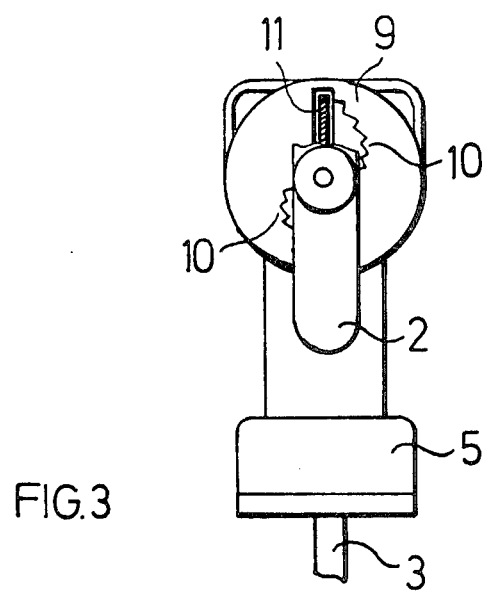
FIG. 3 shows a view from above
Figure 4:
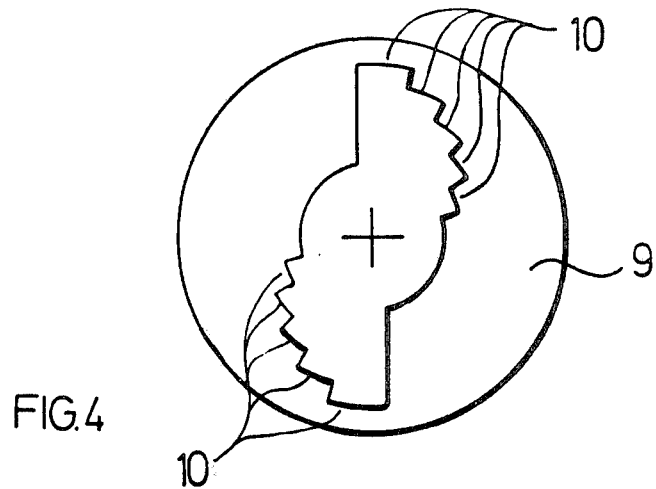
FIG. 4 shows the dose-regulating wheel in detail

The dose-regulating wheel 9 is arranged at the front end of the cylinder casing 8. It is turned about the axis of the cylinder and has stepped notches 10 (see FIG. 4) of varying radial extent. The dose-regulating wheel 9 is provided with engaging cam 14, there being one engaging groove 15 on the cylinder casing 8 to correspond with each notch 10. When the dose-regulating wheel turns one engaging groove 15 comes into action when the corresponding notch 10 moves in a direction about the axis of the mouthpiece 4. A stepped crosspiece 11 is attached to the piston handle 2 above and below the central longitudinal axis thereof (see FIGS. 1, 2, and 3). As the piston handle 2 is pulled to the right in FIG. 1, the crosspiece 11 is drawn into the preselected notch 10 until the corresponding step of the crosspiece 11 rests on the base of this notch. The notches 10 thus form in combination with the crosspiece 11 a variable arresting surface for limiting the piston stroke. The position of the dose regulating wheel determines the extent of the piston stroke and consequently the application amount. As can be seen from FIG. 2 the individual positions of the dose regulating wheel are calibrated in ml according to the volume of the application. The cover plate 12 and piston 1 are provided with a slot-cam-guide (not shown) in order to prevent the piston 1 revolving around the axis of the cylinder. This ensures that the crosspiece 11 attached to the piston handle 2 always aligns with the preselected notch 10 in the dose-regulating wheel 9.

For the application of solutions and suspensions the pistol applicator is screwed on to the supply bottle by means of the screw cap 5. Then the desired application amount is set by turning the dose-regulating wheel 9. Application then takes place, as already described, by pulling the piston handle 2 and releasing some for the returns stroke (see FIG. 2). The pistol applicator has such manageable dimensions that it can be operated with one hand: while the piston handle 2 is pulled the palm of the hand rests on the rear cylinder handhold 13.

What is claimed is:

1. In a pistol applicator for use in veterinary or botanical fields and the like and having a piston operator and a handhold which are drawn towards each other during application and a piston cylinder housing, wherein the improvement comprises adjustable dose-regulating means including a dose-regulating wheel fixed to the cylinder housing and rotatable about the longitudinal axis of the cylinder housing and means defining a plurality of notches in the wheel, each having a different radial extent and an outwardly tapering stepped crosspiece attached to the piston operator and insertable in one preselected notch at a time, wherein one step of the crosspiece is engageable with the means defining a preselected one of the notches when the piston operator is drawn towards the handhold to limit the stroke of the piston operator and thereby regulate the dose applied.

2. Pistol applicator according to claim 1, further comprising a cam on the dose-regulating wheel and grooves in the cylinder which correspond with the notches and which coact with the cam to effect the exact positioning of the regulating wheel for the preselected one notch.

* * * * *